United States Patent [19]

Mazzocchia et al.

[11] Patent Number: 5,254,779
[45] Date of Patent: Oct. 19, 1993

[54] PROCESS FOR OXIDATIVE DEHYDROGENATION OF PROPANE

[76] Inventors: Carlo Mazzocchia; Ezio Tempesti; Chafic Aboumrad, all of Tour Aurore - Place des Reflets, F-92080 Paris La Defense - Cedex 5, France

[21] Appl. No.: 769,488

[22] Filed: Oct. 1, 1991

Related U.S. Application Data

[60] Division of Ser. No. 652,210, Feb. 5, 1991, Pat. No. 5,086,032, which is a continuation of Ser. No. 465,785, Jan. 18, 1990, abandoned.

Foreign Application Priority Data

Jan. 18, 1989 [FR] France ................. 89 00552

[51] Int. Cl.⁵ .............. C07C 2/00; C07C 5/327; C07C 5/370
[52] U.S. Cl. .................... 585/500; 585/654; 585/658; 585/662; 585/663
[58] Field of Search .............. 585/500, 654, 658, 662, 585/663

[56] References Cited

U.S. PATENT DOCUMENTS 3,845,156 10/1974 Farha .................... 502/213

FOREIGN PATENT DOCUMENTS 1197537 7/1970 United Kingdom .

*Primary Examiner*—Patrick P. Garvin
*Assistant Examiner*—E. D. Irzinski
*Attorney, Agent, or Firm*—Finnegan, Henderson, Farabow, Garrett & Dunner

[57] ABSTRACT

A catalyst of the following formula $$Ni_aMoO_x \qquad (I)$$

in which:
  a is a number from 0.6 to 1.3, and
  x is a number determined by the valency requirements of nickel and of molybdenum.

The manufacture of this catalyst comprises the preparation of a solvated precursor and the thermal decomposition of the solvated precursor over a period of from 1 to 4 hours and at a temperature $T_1$ of from 520° to 600° C. The catalyst is utilized in the oxidative dehydrogenation of propane at a temperature of from 400° to 700° C.

16 Claims, No Drawings

PROCESS FOR OXIDATIVE DEHYDROGENATION OF PROPANE

This is a division of application Ser. No. 07/652,210, filed Feb. 5, 1991, now U.S. Pat. No. 5,086,032 which is a continuation of application Ser. No. 06/465,785 filed Jan. 18, 1990, now abandoned.

FIELD OF THE INVENTION

The present invention relates to a catalytic process for dehydrogenation of propane to form the corresponding monoolefin.

BACKGROUND OF THE INVENTION

Numerous catalysts which can be used for the oxidative dehydrogenation of paraffinic hydrocarbons have already been reported in the literature. Thus, there may be mentioned mixed nickel and tin oxides (U.S. Pat. No. 3,745,294 and U.S. Pat. No. 3,801,671), mixed chromium and magnesium oxides (U.S. Pat. No. 3,801,672), and complex oxides combining a metal of group VIII with a metal of group VI B of the periodic table classification and, where appropriate, with a metal of group IV B or of group I A (U.S. Pat. Nos. 3,784,485 and 4,476,339).

West German Patent No. 1,800,063 discloses a process for obtaining mono- or diolefinic hydrocarbons by catalytic oxidative dehydrogenation of butane at a temperature of from 400° to 700° C., which is characterized in that the catalyst employed is a mixture of oxides comprising a molybdenum or tungsten oxide and at least one oxide of a metal chosen from chromium, manganese, iron, nickel and cadmium. This patent recommends, more particularly, the use of mixtures of oxides of molybdenum and nickel in a ratio of molybdenum to nickel of between 4 and 0.04. Example 1 of West German 1,800,063 illustrates the oxidative dehydrogenation of n-butane by means of a catalyst of this kind, obtained from aqueous solutions of ammonium molybdate and of nickel nitrate, which at 590° C. results in a yield of 4.5% of n-butane and of 21% of butadiene. Example 2 of West German 1,800,063 shows that on carrying out the same reaction at 597° C. with an atomic ratio of nickel to molybdenum equal to 0.68, the yields of butadiene and butenes which are obtained are lower than those obtained in Example 1 of the same patent with a Ni/Mo atomic ratio equal to 2.

Furthermore, U.S. Pat. No. 4,131,631 describes a process for dehydrogenation of paraffinic hydrocarbons containing from 3 to 6 carbon atoms to form the corresponding monoolefins, by bringing the hydrocarbon into contact with molecular oxygen, at a temperature of 400° to 700° C. and at a pressure of 1 to 3 atmospheres, over a catalyst of formula:

$$A_aCo_bMo_cO_x$$

in which:
A is an element chosen from phosphorus and the metals of groups IA, IIA, VI and VIII of the periodic table classification,
a is a number from 0 to 3,
b is a number from 0.1 to 2,
c is a number from 0.1 to 6, and
x is a number determined by the valency requirements of the elements A, Co and Mo.

More particularly, Example 8 of U.S. Pat. No. 4,131,631 describes a silica-supported $Co_{0.5}Ni_{0.5}MoO_x$, catalyst subjected to calcination at 593° C. for 24 hours. This catalyst, employed for the oxidative dehydrogenation of propane at 538° C. enables a pass conversion of 13.3% to be attained with a 63.9% selectivity for propylene, which results in a propylene yield of 8.5%. However, a catalyst of this type poses insoluble problems of reproducibility which are due to the presence of silica as the support, and has the disadvantage of an insufficient yield in the case of the oxidative dehydrogenation of propane. Furthermore, the length of its process of manufacture constitutes an obvious economic disadvantage.

SUMMARY OF THE INVENTION

One objective of the present invention comprises, therefore, the development of a reproducible catalyst allowing propane to be oxidatively dehydrogenated in a high yield, in order to overcome the problems with the literature referred to above.

The present invention, accordingly, provides a catalyst for oxidative dehydrogenation of propane. The catalyst has the following formula (I):

$$Ni_aMoO_x \qquad (I)$$

in which:
a is a number approximately from 0.6 to 1.3, and
x is a number determined by the valency requirements of
nickel and of molybdenum.

The present invention also provides a process for the manufacture of a catalyst according to formula (I), comprising the steps of:

(a) reacting ammonium molybdate and nickel nitrate to prepare a solvated precursor of the formula:

$$aNiO.MoO_3.nH_2O.mNH_3$$

wherein
a is a number approximately from 0.6 to 1.3 and
m and n are numbers dependent on the reaction conditions; and (b) subsequently heating and thermally decomposing said solvated precursor over a period of from 1 to 4 hours at a temperature $T_1$ of 520° to 600° C.

The present invention further provides a process for the dehydrogenation of propane to propene, comprising contacting propane with molecular oxygen at a temperature of from 400° to 700° C. and at a pressure not exceeding 0.4 MPa in the presence of a catalyst according to formula (I).

DETAILED DESCRIPTION OF THE INVENTION

A preferred catalyst according to the present invention is $NiMoO_4$, that is, a catalyst according to formula I wherein a=1 and x=4.

The catalyst according to the present invention may comprise, in a mixture, an inert and solid diluent, especially when it is desirable to avoid the creation of hot spots in some regions of the catalyst surface. Silicon carbide (sold under the trademark Carborundum) may be particularly mentioned among these diluents, which may be employed in a proportion of up to approximately 300% by weight of catalyst.

The catalyst according to the present invention is preferably a bulk catalyst, that is to say an unsupported catalyst, so as to solve the abovementioned problems of reproducibility. It preferably has a specific surface which is approximately from 20 to 50 m²/g and, preferably, a mean particle size distribution which is approximately from 50 to 2500 mesh (approximately from 0.1 to 5 mm).

In the abovementioned formula (I) of the catalyst according to the present invention, it is preferable that the ratio x/a, which is the number of oxygen atoms to the number of nickel atoms, be approximately from 3.5 to 6.

The present invention also provides a process for the manufacture of the catalyst of the formula (I) shown above. This process prepares a solvated precursor of the formula:

$$aNiO \cdot MoO_3 nH_2O \cdot mNH_3$$

in which:
a is a number approximately from 0.6 to 1.3, by reaction of ammonium molybdate and of nickel nitrate.

The values for m and n of the solvated precursor are readily determined by one of skill in the art. As is well known to a person skilled in the art, small changes in the parameters of the preparation of the solvated precursor (for example, the pH, the precipitation temperature, the concentration, the filtration temperature, the duration of drying and the temperature of drying) permit the formation of solvated precursors having different values of m and n. Thus, m and n are numbers dependent on the reaction conditions.

The process then thermally decomposes the solvated precursor over a period of approximately 1 to 4 hours and at a temperature $T_1$ of approximately from 520° to 600° C. This thermal decomposition stage in the specified conditions has been found necessary to obtain good catalytic results in the oxidative dehydrogenation of propane as opposed to the use of merely drying in air. Optionally, this process of manufacture may comprise a final stage of thermal activation of the decomposed precursor over a period of approximately from 5 to 30 minutes and at a temperature $T_2$ which is higher than $T_1$, wherein $T_2$ is preferably approximately from 600° to 750° C.

The initial stage of formation of the solvated precursor is well known and can be carried out particularly by mixing solutions of ammonium molybdate and of nickel nitrate with stirring at a temperature which is approximately from 65° to 90° C. and at a pH of approximately 5.6. As is well known to a person skilled in the art, small changes in the parameters of this preparation (for example the pH, the precipitation temperature, the concentration, the filtration temperature, the duration of drying and the temperature of drying) permit the formation of solvated precursors having different values of a, m and n. For example, in one embodiment, solvated precursors have been prepared wherein n is a number less than or equal to 1 and m is a number from 0 to less than 1, by drying the precursor at 120° C. for approximately 5 hours.

As is obvious in the case of the techniques of thermal decomposition (temperature $T_1$) and thermal activation (temperature $T_2$), the duration of these stages is proportionately shorter the higher the temperature selected for the thermal treatment ($T_1$ and $T_2$) The applicants have found that the longest duration of the combined thermal treatment according to the present invention is five times shorter than that described by U.S. Pat. No. 4,131,631.

The present invention also provides a process for the dehydrogenation of propane comprising bringing propane into contact with molecular oxygen at a temperature of approximately from 400° to 700° C., and preferably from 550° to 650° C., and at a pressure not exceeding approximately 0.4 MPa (approximately 4 atmospheres) in the presence of a catalyst which has the formula (I) described above or which is obtained by the process of manufacture described above. The apparent contact time employed in this process may be selected from a range extending from 0.01 to 30 seconds, and preferably from 0.1 to 5 seconds. The process according to the invention may be carried out in the presence of molecular oxygen or of a gas containing molecular oxygen, such as air. The molar ratio of propane to oxygen in the process according to the invention is preferably from 0.1 to 30, and more preferably from 0.5 to 10. The reaction mixture may, furthermore, be diluted with at least one inert gas such as nitrogen, carbon dioxide, steam, and the like. The concentration of propane in the reaction mixture can, without any disadvantage, be as much as 25 mol %.

The oxidative dehydrogenation process according to the invention may be carried out either in a conventional reactor, such as a stationary-bed reactor or a fluidized-bed reactor.

The specific examples below will enable the invention to be better understood. However, they are given merely by way of guidance and do not imply any limitation.

EXAMPLES 1 and 2

Preparation of the Catalyst (A)

Two equimolar solutions of ammonium molybdate and of nickel nitrate were mixed at pH 5.6 and at a temperature of 85° C., so as to obtain a precipitated precursor of the formula:

$$NiO \cdot MoO_3 \cdot nH_2O \cdot mNH_3$$

wherein m and n are numbers dependent on the reaction conditions. The precipitated precursor was dried at 120° C. for five hours to obtain a precipitated precursor of the formula $$NiO \cdot MoO_3 \cdot nH_2O \cdot mNH_3$$

in which:
n is a number less than or equal to 1, and
m is a number from 0 to less than 1.

This precursor was then decomposed thermally for two hours at 550° C., so as to obtain a catalyst (A) of formula $NiMoO_4$ with a specific surface of 40 m²/g.

The oxidative dehydrogenation of propane employed a horizontal tubular quartz reactor, 30 cm³ in total volume, connected to four mass-flowmeters fed successively with nitrogen, oxygen, propane and air. 0.5 g of catalyst (A) mixed with 10 g of Carborundum (SiC) powder was confined in the central part of the reactor between two Carborundum plugs of coarse particle size and two quartz wool plugs at the ends. There was a quartz sheath installed in the middle of the catalyst making it possible to introduce a thermocouple and to measure the actual temperature of the catalyst bed. Heating was provided by electrical resistors in the reactor chamber, where the conductor was continually agitated hot air. The propane/oxygen molar ratio was equal to 0.9.

The components of the reaction mixture were passed over the catalyst bed at a rate of 15 normal liters per hour and a temperature T° C. which is shown in the table below. The reaction products were cooled to 100° C. before being analyzed by gas phase chromatography to determine their composition and especially the concentration of propylene.

The molar conversion shown in the table below, and expressed in %, represents the total propane converted to propylene and to other products (pass conversion); the selectively for propylene shown in the table below represents the percentage of propylene obtained relative to the propane converted; and finally, the yield (pass molar conversion to propane) shown in the table below represents the percentage of propane converted to propylene. The table below shows the results obtained as a function of the reaction temperature.

EXAMPLES 3 and 4

Preparation of the Catalyst (B)

After having been mixed with the Carborundum (SiC) powder and installed in the reactor, the catalyst (A) was subjected to a thermal activation. To do this, the reactor was heated to 700° C. over 25 minutes in the presence of oxygen and was then left for 5 minutes at 700° C. before cooling to the reaction temperature. An activated catalyst (B) was thus obtained which was employed in the same conditions as in the preceding examples. The table below shows the results obtained as a function of the reaction temperature.

EXAMPLE 5

Preparation of the Catalyst (C)

The procedure for the preparation of the catalyst (A) was reproduced, with the following exception: the solutions of ammonium molybdate and of nickel nitrate were mixed at a temperature of 70° C. at pH 5.6 and the precipitate formed was then left to stand until it had an excess quantity of molybdic anhydride, such that, after thermal decomposition at over two hours at 550° C., the catalyst (C) obtained had the formula $NiMo_{1.5}O_{5.5}$. This catalyst had a specific surface of 27 m²/g. It was employed under the same conditions as in Examples 2 and 4. The results obtained appear in the table below.

EXAMPLE 6 (Comparative)

Preparation of the Catalyst (D)

The procedure for the preparation of the catalyst (A) was reproduced with the following exception: the solutions of ammonium molybdate and of nickel nitrate were mixed at a temperature of 85° C. at pH 6. Because of the coprecipitation of a compound with an excess of nickel, a green-colored precursor was obtained which, after thermal decomposition at over two hours at 550° C., formed a catalyst (D) of formula $Ni_{1.5}MoO_{4.5}$ with a specific surface of 30 m²/g. This catalyst was employed under the same conditions as in the preceding examples. The results obtained appear in the table below.

TABLE

| Example | T | Conversion (%) | Selectively (%) | Yield (%) |
|---|---|---|---|---|
| 1 | 560 | 23.3 | 50.6 | 11.8 |
| 2 | 600 | 37.1 | 33.8 | 12.5 |

TABLE-continued

| Example | T | Conversion (%) | Selectively (%) | Yield (%) |
|---|---|---|---|---|
| 3 | 560 | 16.8 | 80.3 | 13.5 |
| 4 | 600 | 29.0 | 62.5 | 18.1 |
| 5 | 600 | 37.2 | 28.6 | 10.6 |
| 6 | 600 | 34.0 | 18.5 | 6.3 |

We claim:

1. A process for the dehydrogenation of propane to propene, comprising contacting propane with molecular oxygen at a temperature of from 400° to 700° C. and at a pressure not exceeding 0.4 MPa in the presence of a catalyst of the following formula:

$$, Ni_aMoO_x \qquad (I)$$

in which:
  a is a number from 0.6 to 1.3, and
  x is a number determined by the valency requirements of nickel and of molybdenum.

2. A process according to claim 1, wherein the molar ratio of propane to oxygen is from 0.1 to 30.

3. A process according to claim 2, wherein the reaction mixture is diluted with at least one inert gas and wherein the concentration of propane in said mixture is less than or equal to 25 mol %.

4. A process according to claim 1, wherein the reaction mixture is diluted with at least one inert gas and wherein the concentration of propane in said mixture is less than or equal to 25 mol %.

5. A process for the dehydrogenation of propane to propene, comprising contacting propane with molecular oxygen at a temperature of from 400° to 700° C. and at a pressure not exceeding 0.4 MPa in the presence of at catalyst of the following formula:

$$Ni_aMoO_x \qquad (I)$$

in which:
  a is a number from 0.6 to 1.3, and
  x is a number determined by the valency requirements of nickel and of molybdenum,
wherein the catalyst further comprises an inert solid diluent in a mixture.

6. A process according to claim 5, wherein the molar ratio of propane to oxygen is from 0.1 to 30.

7. A process according to claim 6, wherein the reaction mixture is diluted with at least one inert gas and wherein the concentration of propane in said mixture is less than or equal to 25 mol %.

8. A process according to claim 5, wherein the reaction mixture is diluted with at least one inert gas and wherein the concentration of propane in said mixture is less than or equal to 25 mol %.

9. A process according to claim 1, wherein said catalyst is prepared by heating and thermally decomposing a solvated precursor of the formula:

$$aNiO.MoO_3.nH_2O.mNH_3$$

wherein m and n are number dependent upon the reaction conditions.

10. A process according to claim 9, wherein said step of heating and thermally decomposing takes place at a temperature of about 520° to 600° C.

11. A process according to claim 9, further comprising the step of thermally activating the decomposed precursor.

12. A process according to claim 11, wherein said step of thermally activating takes place at a temperature of about 600° to 750° C.

13. A process according to claim 5, wherein said catalyst is prepared by heating and thermally decomposing a solvated precursor of the formula:

$$aNiO \cdot MoO_3 \cdot nH_2O \cdot mNH_3$$

wherein m and n are numbers dependent upon the reaction conditions.

14. A process according to claim 13, wherein said step of heating and thermally decomposing takes place at a temperature of about 520° to 600° C.

15. A process according to claim 13, further comprising the step of thermally activating the decomposed precursor.

16. A process according to claim 14, wherein said step of thermally activating takes place at a temperature of about 600° to 750° C.

* * * * *

UNITED STATES PATENT AND TRADEMARK OFFICE
CERTIFICATE OF CORRECTION

PATENT NO.   : 5,254,779
DATED        : October 19, 1993
INVENTOR(S)  : Carlo MAZZOCCHIA et al.

It is certified that error appears in the above-indentified patent and that said Letters Patent is hereby corrected as shown below:

Claim 1, col. 6, in formula (1) before the formula, delete --,--.

Claim 5, col. 6, line 37, change "at" to --a--.

Signed and Sealed this

Nineteenth Day of April, 1994

*Attest:*

BRUCE LEHMAN

*Attesting Officer*   Commissioner of Patents and Trademarks